US010973881B2

(12) United States Patent
Jung et al.

(10) Patent No.: US 10,973,881 B2
(45) Date of Patent: Apr. 13, 2021

(54) IGG4 FC FRAGMENT COMPRISING MODIFIED HINGE REGION

(71) Applicant: HANMI PHARM. CO., LTD., Hwaseong-si (KR)

(72) Inventors: Sung Youb Jung, Suwon-si (KR); Yong Ho Huh, Seoul (KR); Sung Hee Park, Seongnam-si (KR); Jong Soo Lee, Seongnam-si (KR); In Young Choi, Yongin-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 406 days.

(21) Appl. No.: 14/894,222

(22) PCT Filed: May 29, 2014

(86) PCT No.: PCT/KR2014/004799
§ 371 (c)(1),
(2) Date: Nov. 25, 2015

(87) PCT Pub. No.: WO2014/193173
PCT Pub. Date: Dec. 4, 2014

(65) Prior Publication Data
US 2016/0129129 A1    May 12, 2016

(30) Foreign Application Priority Data

May 31, 2013 (KR) .......................... 10-2013-0063029

(51) Int. Cl.
| | | |
|---|---|---|
| *C07K 19/00* | (2006.01) | |
| *A61K 47/68* | (2017.01) | |
| *A61K 38/19* | (2006.01) | |
| *C07K 14/47* | (2006.01) | |
| *A61K 47/60* | (2017.01) | |
| *C07K 16/28* | (2006.01) | |

(52) U.S. Cl.
CPC ............ *A61K 38/193* (2013.01); *A61K 47/60* (2017.08); *A61K 47/68* (2017.08); *A61K 47/6813* (2017.08); *A61K 47/6849* (2017.08); *C07K 14/47* (2013.01); *C07K 16/2803* (2013.01); *C07K 2317/40* (2013.01); *C07K 2317/52* (2013.01); *C07K 2317/53* (2013.01); *C07K 2317/94* (2013.01); *C07K 2319/30* (2013.01)

(58) Field of Classification Search
CPC .............. A61K 38/193; A61K 47/6849; A61K 47/6813; A61K 47/68; A61K 47/60; C07K 14/47; C07K 16/2803; C07K 2319/30; C07K 2317/52; C07K 2317/40; C07K 2317/94; C07K 2317/53; A61P 43/00
See application file for complete search history.

(56) References Cited

U.S. PATENT DOCUMENTS

| | | | | |
|---|---|---|---|---|
| 5,349,053 | A | 9/1994 | Landolfi | |
| 5,585,097 | A | 12/1996 | Bolt et al. | |
| 7,608,429 | B2 * | 10/2009 | Reilly | C07K 16/22 435/69.6 |
| 7,968,316 | B2 * | 6/2011 | Jung | C07K 16/00 435/320.1 |
| 8,043,616 | B2 * | 10/2011 | Anderson | C07K 14/70503 424/134.1 |
| 8,802,091 | B2 * | 8/2014 | Johnson | A61K 39/39558 424/130.1 |
| 9,834,597 | B2 * | 12/2017 | Francis | C07K 16/18 |
| 2006/0084145 | A1 * | 4/2006 | Anderson | C07K 14/70503 435/69.1 |
| 2007/0004909 | A1 * | 1/2007 | Johnson | C07K 16/283 530/388.8 |
| 2007/0243194 | A1 * | 10/2007 | Hariharan | C07K 16/2863 424/143.1 |
| 2010/0226925 | A1 * | 9/2010 | Dillon | C07K 16/00 424/141.1 |
| 2012/0100140 | A1 | 4/2012 | Reyes et al. | |
| 2012/0276097 | A1 | 11/2012 | Yang et al. | |
| 2014/0357843 | A1 * | 12/2014 | Oh | C07K 16/00 530/387.3 |

FOREIGN PATENT DOCUMENTS

| | | | |
|---|---|---|---|
| JP | 2009-513110 A | 4/2009 | |
| JP | 2012-224635 A | 11/2012 | |
| KR | 10-2006-0106486 | 10/2006 | |
| WO | 2005/047334 A1 | 5/2005 | |
| WO | 2005/047336 A1 | 5/2005 | |
| WO | WO-2006113665 A2 * | 10/2006 | ........... C07K 16/283 |
| WO | 2007/021129 A1 | 2/2007 | |
| WO | WO-2010106180 A2 * | 9/2010 | ............. C07K 16/00 |
| WO | 2012/022982 A2 | 2/2012 | |

(Continued)

OTHER PUBLICATIONS

Stubenrauch et al., Drug Metabolism and Disposition 38(1): 84-91 (Year: 2010).*

(Continued)

*Primary Examiner* — Phuong Huynh
(74) *Attorney, Agent, or Firm* — Sughrue Mion, PLLC

(57) ABSTRACT

The present invention relates to a modified IgG4 Fc fragment useful as a drug carrier. When the modified IgG4 Fc fragment of the present invention is combined with an arbitrary drug, the resulting drug conjugate can minimize the effector functions of the IgG4 Fc and the chain exchange with in vivo IgG while maintaining in vivo activity and improving in vivo duration of the drug conjugate.

12 Claims, 2 Drawing Sheets

Specification includes a Sequence Listing.

(56) References Cited

FOREIGN PATENT DOCUMENTS

| WO | 2012/083370 A1 | 6/2012 |
| WO | 2013/012733 A1 | 1/2013 |
| WO | 2013/124450 A1 | 8/2013 |
| WO | 2013/124451 A1 | 8/2013 |

OTHER PUBLICATIONS

Burgess et al., Journal of Cell Biology, vol. 111, pp. 2129-2138 (Year: 1990).*

Skolnick et al., Trends in Biotechnology, vol. 18, pp. 34-39 (Year: 2000).*

Korean Patent Office, Communication dated Aug. 22, 2017 by the Korean Patent Office in copending Application No. 10-2013-0063029.

Schuurman et al., "The inter-heavy chain disulfide bonds of IgG4 are in equilibrium with intra-chain disulfide bonds", Molecular Immunology, 38, 2001, pp. 1-8.

Russian Patent and Trademark Office, Communication dated Jan. 17, 2018 in counterpart application No. 2015153162/10(081963).

Marijn Van Der Neut Kolfschoten et al., "Anti-Inflammatory Activity of Human IgG4 Antibodies by Dynamic Fab Arm Exchange", Science, Sep. 14, 2007, pp. 1554-1557, vol. 317.

Michael S. Cole, et al., "Human IgG2 Variants of Chimeric Anti-CD3 Are Nonmitogenic to T Cells", The Journal of Immunology, 1997, pp. 3613-3621, vol. 159.

International Searching Authority, International Search Report for PCT/KR2014/004799 dated Sep. 2, 2014.

Japanese Patent Office; Communication dated May 1, 2018 in counterpart JP application No. 2016-516448.

Russian Patent Office; Communication dated Jun. 14, 2018 in counterpart RU application No. 2015153162/10.

European Office Action; Communication dated Aug. 22, 2019 in counterpart EP Application No. 18 168 489.5.

Communication dated Sep. 4, 2020, issued by the Australian Patent Office in counterpart Australian Application No. 2020202581.

* cited by examiner

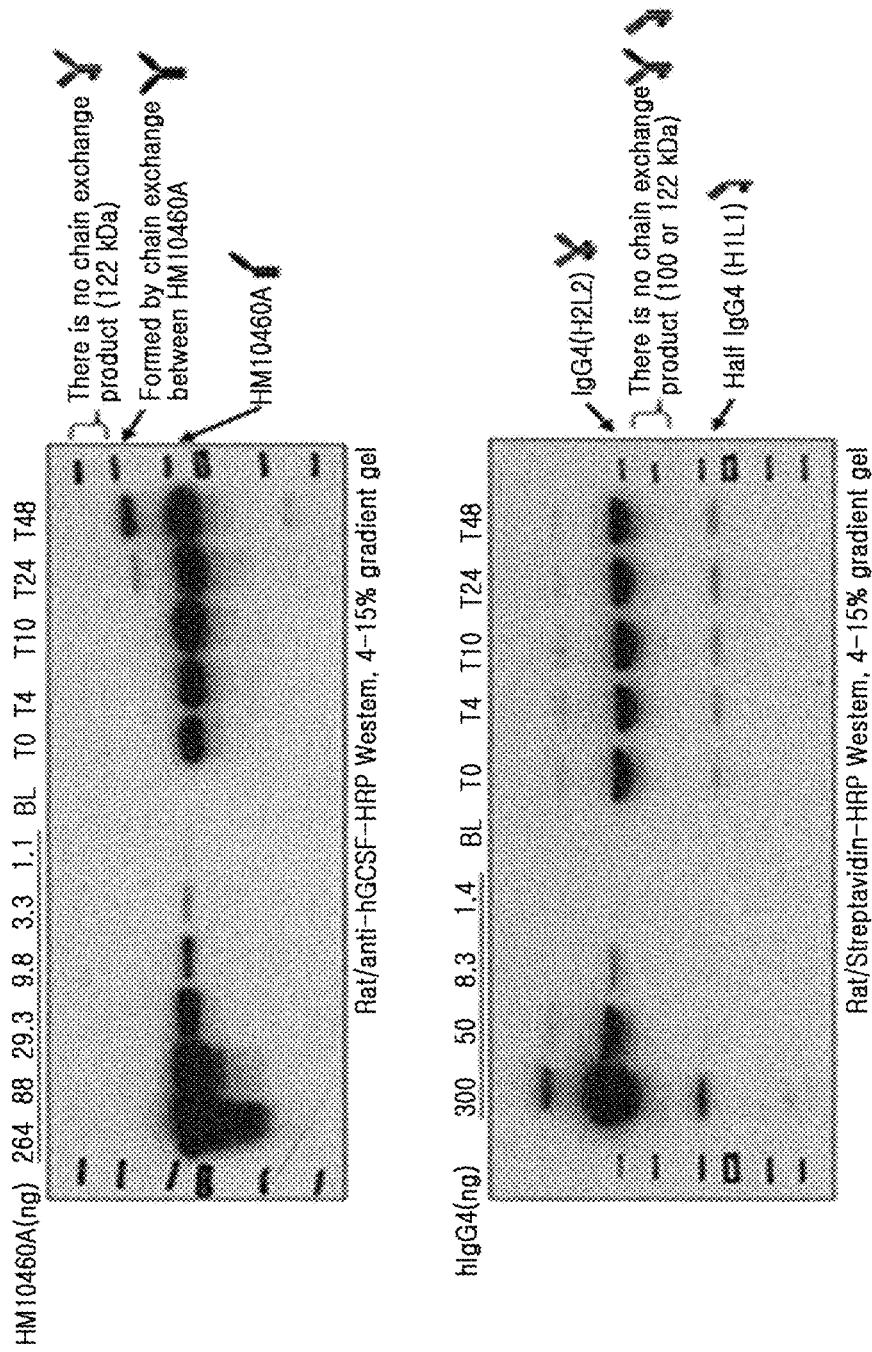
[FIG. 1]

[FIG.2]
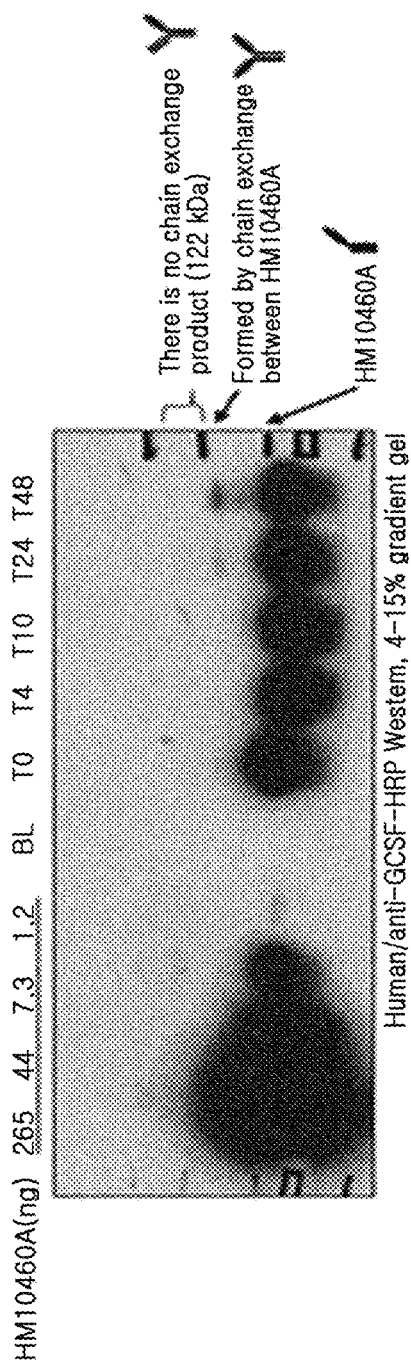

IGG4 FC FRAGMENT COMPRISING MODIFIED HINGE REGION

CROSS REFERENCE TO RELATED APPLICATIONS

This application is a National Stage of International Application No. PCT/KR2014/004799 filed May 29, 2014, claiming priority based on Korean Patent Application No. 10-2013-0063029 filed May 31, 2013, the contents of all of which are incorporated herein by reference in their entirety.

TECHNICAL FIELD

The present invention relates to an IgG4 Fc fragment useful as a drug carrier, and more specifically, to an IgG4 Fc fragment which can minimize the effector functions by the Fc but does not induce a chain exchange with in vivo IgG, and can improve in vivo half-life of a conjugated drug.

BACKGROUND ART

Advancement in genetic engineering technology has led to the manufacture and utilization of various kinds of protein drugs. However, proteins drugs have fatal problems in that they are easily denatured or easily decomposed by in vivo proteases and thus cannot maintain their in vivo concentrations or titers for a long period of time. Therefore, it is very important to maintain the blood and in vivo concentrations of protein drugs at an appropriate level by increasing protein stability in order to provide effective treatment to patients while reducing the patients' burden to receive frequent protein supplies by injections, etc., and the expenses thereof.

Accordingly, for the improvement of in vivo stability of protein drugs, various attempts have been made for a long time, by changing the formulation type of proteins, fusion with other proteins, or attaching an appropriate polymer on protein surfaces by chemical or biological methods.

One of the attempts to improve protein stability by fusion with other proteins is to perform a fusion between immunoglobulin Fc and a protein.

The Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In this regard, active studies have been performed to improve therapeutic proteins through the fusions between the Fc region and therapeutic proteins.

However, the Fc fusion proteins produced by genetic recombination have disadvantages in that a protein fusion is possible only in a particular area of the Fc region, i.e., an amino-terminus or carboxy-terminus, and only between glycosylated proteins or between aglycosylated proteins, but it is impossible between a glycosylated protein and an aglycosylated protein. Additionally, the Fc fusion proteins produced by genetic recombination have problems in that an immune response may occur due to the amino acid sequence newly produced by a fusion and also that the sensitivity of a proteinase on the linker area may be increased.

Additionally, the fusion proteins with the Fc have an increased target protein serum half-life, but at the same time they also has a problem in that the effector functions possessed by the Fc region are exhibited (U.S. Pat. No. 5,349,053). By the effector functions of the Fc region, the fusion proteins can fix complements or bind to FcRs-expressing cells to destroy particular cells, and induce production and secretion of various cytokines which induce inflammation, thereby inducing inflammation. Additionally, the protein sequences in the fused areas are new protein sequences which are not present in human body, and thus they have various drawbacks including a possible induction of immune responses in the case of a long-term administration.

Accordingly, studies have been focused on utilizing immunoglobulins or immunoglobulin fragments in which the effector functions were deleted while serum half-lives were maintained. Cole et al. previously reported that ADCC activity was inhibited by substituting the $234^{th}$, $235^{th}$, and $237^{th}$ residues in the CH2 domain, which are known to play an important role in binding to Fc receptors, with alanine, for the production of Fc derivatives with reduced affinities on Fc receptors (Cole et al., J. Immunol. 159: 3613-3621, 1997). However, all these have inappropriate amino acids which are different from those in the native human Fc region and may thus have a higher immunity or antigenicity, and preferable Fc functions may be lost.

As a method for removing or reducing unwanted effector functions while maintaining high blood concentration of immunoglobulins, a method of removing saccharides in immunoglobulins was studied. In U.S. Pat. No. 5,585,097, aglycosylated antibody derivatives were prepared by substituting the asparagine residue at position 297 of the CH2 domain, which is the glycosylated residue of CD3 antibodies, with another amino acid when preparing CD3 antibodies, and in particular, the derivatives showed reduced effector functions while maintaining the binding force with FcRn receptors without alteration in their serum half-lives. However, this method also has a problem in that they may be recognized as foreign materials and rejected as such by the immune system, due to the production of a new recombinant construct.

In preparing protein fusions using sequences of native IgG Fc, IgG4 Fc may be selected in order to minimize the effector functions by Fc. IgG4 has been known to have an in vivo half-life similar to that of IgG1 but has relatively small effector functions due to the difference in the amino acid sequence. However, despite the advantage of IgG4 having reduced effector functions, an in vivo chain exchange may occur between IgG4 due to its peculiar hinge sequence, and thus it was reported that there is much difficulty when using protein fusions for therapeutic purposes (van der Neut Kolfschoten, et al., Science, 317:1554-1557, 2007). That is, there is a problem in that, when IgG4 Fc is used as a carrier for a protein fusion, a chain exchange with IgG4 present in vivo occurs, thereby forming a hybrid with native IgG4, or it may be present in the form of monomers thereby altering the original structure and having a structure with low therapeutic activity. This is a common problem whether the fusion product between an IgG4 Fc fragment and a physiologically active material is produced via genetic engineering or in vitro.

DISCLOSURE

Technical Problem

Under the circumstances, the present inventors, as a result of studies to develop an IgG Fc fragment capable of acting as a drug carrier, which has a low risk of inducing Fab arm exchange reaction with in vivo IgG and effector functions while being capable of overcoming the disadvantages in fusion technology of genetic recombination, discovered that a drug conjugate with improved durability but without the risk of inducing the Fab arm exchange reaction with in vivo IgG and effector functions could be formed when the hinge sequence of the IgG4 Fc fragment, which was mutated to have only one cysteine residue, was produced in *E. coli* and conjugated with a drug, thereby completing the present invention.

Technical Solution

An object of the present invention is to provide an IgG4 Fc fragment, which has a low risk of inducing a chain exchange reaction with in vivo IgG or effector functions and can act as a drug carrier. More specifically, an object of the present invention is to provide a modified IgG4 Fc fragment including a modified hinge region, wherein part of the hinge sequence is deleted to include only one cysteine residue.

Another object of the present invention is to provide a nucleic acid which encodes a modified IgG4 Fc fragment including a modified hinge region, wherein part of the hinge sequence is deleted to include only one cysteine residue.

Still another object of the present invention is to provide a vector including a nucleic acid which encodes a modified IgG4 Fc fragment including a modified hinge region, wherein part of the hinge sequence is deleted to include only one cysteine residue.

Still another object of the present invention is to provide a microorganism introduced with a vector including a nucleic acid which encodes a modified IgG4 Fc fragment including a modified hinge region, wherein part of the hinge sequence is deleted to include only one cysteine residue.

Still another object of the present invention is to provide a method for preparing a modified IgG4 Fc fragment including culturing the microorganism, which is introduced with a vector including a nucleic acid that encodes the modified IgG4 Fc fragment.

Still another object of the present invention is to provide a drug conjugate, wherein a drug and a modified IgG4 Fc fragment are conjugated by a linker.

Still another object of the present invention is to provide a pharmaceutical composition including a drug conjugate, wherein a drug and a modified IgG4 Fc fragment are conjugated by a linker.

Advantageous Effects of the Invention

The present invention can provide a modified IgG4 Fc fragment which has a minimized effector function without substitution or addition of amino acids or glycan addition and also has no chain exchange reaction with in vivo IgG4. The modified IgG4 Fc fragment of the present invention, regardless of the method of conjugating it to a drug, such as a genetic engineering method and an in vitro covalent method, can inhibit an in vivo chain exchange reaction of a conjugated drug when it is conjugated to a drug, and can thereby provide significant therapeutic superiority compared to the native IgG4 Fc fragment.

BRIEF DESCRIPTION OF THE DRAWINGS

FIG. 1 shows the presence/absence of human IgG4 chain exchange between biotinylated hIgG4 and a human granulocyte colony-stimulating factor-PEG-IgG4 Fc fragment conjugate in rat blood.

FIG. 2 shows the presence/absence of human IgG4 chain exchange between biotinylated hIgG4 and a human granulocyte colony-stimulating factor-PEG-IgG4 Fc fragment conjugate in human blood.

BEST MODE

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

In an aspect to accomplish the above objects, the present invention provides a modified IgG4 Fc fragment useful as a drug carrier. More specifically, the present invention provides a modified IgG4 Fc fragment including a modified hinge region, wherein part of the hinge sequence is deleted to include only one cysteine residue.

The modified IgG4 Fc fragment of the present invention includes a modified hinge region, wherein part of the hinge region represented by the following amino acid sequence is deleted to include only one cysteine residue:

(SEQ ID NO: 1)
Glu-Ser-Lys-Tyr-Gly-Pro-Pro-Cys-Pro-Ser-Cys-Pro.

The present inventors, while endeavoring to solve the problem of the IgG4 Fc fragment having low usefulness due to the chain exchange reaction with in vivo IgG4, despite its usefulness as a carrier for increasing half-lives of drugs, discovered that the in vivo chain exchange reaction and monomer formation did not occur when the IgG4 Fc fragment was modified by removing, via deletion, one cysteine residue from the two cysteine residues present in the hinge region of the IgG4 Fc fragment as well as part of the hinge region, thereby confirming that the modified IgG4 Fc fragment can be effectively used as a drug carrier.

In an embodiment, the IgG4 Fc fragment of the present invention may include a hinge region which was modified by the deletion of 1 to 8 amino acid(s) including a Cys residue at the $8^{th}$ position of an amino acid sequence of SEQ ID NO: 1.

Additionally, in an embodiment, the IgG4 Fc fragment of the present invention may include a hinge region which was modified by the deletion of 1 to 8 amino acid(s) including a Cys residue at the $11^{th}$ position of an amino acid sequence of SEQ ID NO: 1.

Alternatively, in an embodiment, the IgG4 Fc fragment of the present invention may include a hinge region which was modified by the deletion of 1 to 5 amino acid(s) including a Cys residue at the $8^{th}$ position or 1 to 5 amino acid(s) including a Cys residue at the $11^{th}$ position of an amino acid sequence of SEQ ID NO: 1.

Alternatively, in an embodiment, the IgG4 Fc fragment of the present invention may include a hinge region which was modified by the deletion of 1 to 3 amino acid(s) including a Cys residue at the $8^{th}$ position or 1 to 3 amino acid(s) including a Cys residue at the $11^{th}$ position of an amino acid sequence of SEQ ID NO: 1.

The amino acid residues deleted above may be continuous or discontinuous.

The hinge region of the IgG4 Fc fragment of the present invention is characterized in that it is modified to include only one cysteine residue between the two cysteine residues at the 8th and 11th positions of the amino acid sequence of SEQ ID NO: 1, and in that not both of the two cysteine residues are removed.

The hinge region modified to include only one cysteine residue out of the two cysteine residues within the hinge region renders the effects without in vivo chain exchange, monomer formation, etc., on the modified IgG4 Fc fragment.

As used herein, the term "carrier" refers to a material which is conjugated to a drug, and being conjugated to a drug, it generally increases or removes physiological activities of the drug. However, the carrier of the present invention increases in vivo stability of a drug while simultaneously minimizing the decrease in the physiological activities of the drug, and the carrier of the present invention is characterized in that it does not have any pharmacological effects of preventing therapeutic activities of the drug conjugated to the carrier, such as apoptosis or complement activation, and binding with a particular protein.

As used herein, the term "IgG4 Fc fragment" refers to a heavy chain constant region 2 (CH2) and a heavy chain constant region 3 (CH3), excluding heavy and light chain variable regions, a heavy chain constant region 1 (CH1) and a light chain constant region 1 (CL1) of IgG4, but including a modified hinge region in the heavy chain constant region. Additionally, the IgG4 Fc fragment of the present invention may refer to an extended Fc region including a part or the entirety of the heavy chain constant region 1 (CH1) and/or the light chain constant region 1 (CL1), excluding the heavy and light chain variable regions of the immunoglobulin, insofar as the IgG4 Fc fragment has substantially the same effect as or an improved effect compared to that of the native type.

Additionally, the IgG4 Fc fragment of the present invention includes not only its native amino acid sequence but also a sequence derivative thereof (mutein). As used herein, the term "a mutein of IgG4 Fc fragment" refers to an IgG4 Fc fragment having an amino acid sequence different from its native type by deletion, insertion, conservative substitution, non-conservative substitution, or a combination thereof, of at least one amino acid residue in the native amino acid sequence in the region excluding its hinge region. Additionally, various types of derivatives which have a removal of a region capable of forming a disulfide bond, a removal of a few amino acids from the N-terminus of the native Fc, or an addition of a methionine residue to the N-terminus of the native Fc may be possible. Additionally, the complement-binding region, e.g., the C1 q-binding region or ADCC region, may be removed for elimination of effector functions. The methods for preparing the muteins of the Fc region are disclosed in International Patent Publications WO 97/34631, WO 96/32478, etc.

The amino acid exchange in proteins or peptides without complete alteration of the activity of molecules was previously disclosed (H. Neurath, R. L. Hill, The Proteins, Academic Press, New York, 1979). The commonly occurring exchanges are the exchange between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In certain circumstances, modification may be performed by phosphorylation, sulfation, acrylation, glycosylation, methylation, farnesylation, acetylation, amidation, etc.

Meanwhile, the IgG4 Fc fragment of the present invention may be one derived from humans, cattle, goats, pigs, mice, rabbits, hamsters, rats, guinea pigs, etc., and preferably from humans.

The IgG4 Fc fragment of the present invention may be a recombinant type of IgG4 Fc fragment in which the Fc region, derived from humans, cattle, goats, pigs, mice, rabbits, hamsters, rats, guinea pigs, etc., was obtained from a microorganism.

Additionally, the IgG4 Fc fragment may be in the form of native glycans, glycans with an increased number compared to the native glycan, or one without glycans. The increase, decrease, or removal of Fc glycans in immunoglobulins may be performed using a conventional method such as a chemical method, an enzymatic method, a genetic engineering method using microorganisms, etc. In particular, since the immunoglobulin Fc region, where glycans are removed from Fc, shows a significant deterioration in binding capacity of the complement (c1q) and a decrease or elimination of antibody-dependent cytotoxicity or complement-dependent cytotoxicity, unnecessary in vivo immune responses are not induced. In this regard, a more appropriate type of IgG4 Fc fragment that better meets the original purpose as a drug carrier may be an aglycosylated IgG4 Fc fragment.

As used herein, the term "deglycosylation" refers to an Fc region in which saccharides are removed by an enzyme, and "aglycosylation" refers to an aglycosylated Fc fragment produced in a prokaryotic cell, and preferably in E. coli.

Additionally, the IgG4 Fc fragment of the present invention may be one modified by a non-peptide polymer. Preferably, the IgG4 Fc fragment of the present invention may be one modified by polyethylene glycol. The IgG4 Fc fragment modified by polyethylene glycol may be prepared by reacting with polyethylene glycol at pH 7 or higher, preferably at pH 7.5 to pH 9, and more preferably at pH 8.0.

As used herein, the term "a modified hinge region" refers to a hinge region in which any one cysteine residue out of the cysteine residues at the 8th and 11th positions of an amino acid sequence of SEQ ID NO: 1, which is the sequence of the hinge region of a native IgG4 Fc fragment, was deleted, and additionally, part of the amino acid was further deleted.

In the present invention, the number of amino acid residues deleted in the hinge region may be in the range of 1 to 8, and in particular, the amino acid residue(s) may be continuous or discontinuous. Specifically, for example, the modified hinge region of the present invention may include a deletion in only one cysteine residue at the 8th position or at the 11th position; or a deletion of 2 to 8 continuous or discontinuous amino acids including the cysteine reside at the 8th position; or a deletion of 2 to 8 continuous or discontinuous amino acids including the cysteine reside at the 11th position.

The modified hinge region of the present invention may have, for example, at least one amino acid sequence among the amino acid sequences shown below:

(SEQ ID NO: 4)
Glu-Ser-Lys-Tyr-Gly-Pro-Pro-Pro-Ser-Cys-Pro, (SEQ ID NO: 5)
Glu-Ser-Lys-Tyr-Gly-Pro-Pro-Cys-Pro-Ser-Pro, (SEQ ID NO: 6)
Glu-Ser-Lys-Tyr-Gly-Pro-Pro-Cys-Pro-Ser, (SEQ ID NO: 7)
Glu-Ser-Lys-Tyr-Gly-Pro-Pro-Cys-Pro-Pro, (SEQ ID NO: 8)
Lys-Tyr-Gly-Pro-Pro-Cys-Pro-Ser,

-continued

Glu-Ser-Lys-Tyr-Gly-Pro-Pro-Cys, (SEQ ID NO: 9)

Glu-Lys-Tyr-Gly-Pro-Pro-Cys, (SEQ ID NO: 10)

Glu-Ser-Pro-Ser-Cys-Pro, (SEQ ID NO: 11)

Glu-Pro-Ser-Cys-Pro, (SEQ ID NO: 12)

Pro-Ser-Cys-Pro, (SEQ ID NO: 13)

Glu-Ser-Lys-Tyr-Gly-Pro-Pro-Ser-Cys-Pro, (SEQ ID NO: 14)

Lys-Tyr-Gly-Pro-Pro-Pro-Ser-Cys-Pro, (SEQ ID NO: 15)

Glu-Ser-Lys-Tyr-Gly-Pro-Ser-Cys-Pro, (SEQ ID NO: 16)

Glu-Ser-Lys-Tyr-Gly-Pro-Pro-Cys, (SEQ ID NO: 17)

Lys-Tyr-Gly-Pro-Pro-Cys-Pro, (SEQ ID NO: 18)

Glu-Ser-Lys-Pro-Ser-Cys-Pro, (SEQ ID NO: 19)

Glu-Ser-Pro-Ser-Cys-Pro, and (SEQ ID NO: 20)

Glu-Pro-Ser-Cys. (SEQ ID NO: 21)

In an exemplary embodiment of the present invention, in order to examine the chain exchange mechanism between the IgG4 present in the rat blood and human blood and the conjugate between the modified IgG4 Fc fragment and a physiologically active protein according to the present invention, rat blood and human blood were respectively mixed with the conjugate between the IgG4 Fc and the physiologically active protein, and samples were collected according to each time zone and subjected to Western blot analysis using antibodies to the physiologically active protein. As a result, it was confirmed that molecules that may be produced by the chain exchange with rat IgG4 or human IgG4 were not produced.

Accordingly, when the modified IgG4 Fc fragment according to the present invention is used as a carrier for drugs, it can be effectively used to increase serum half-lives of drugs and improve physiological activities of drugs without an exchange with in vivo native immunoglobulins.

According to another aspect, the present invention provides a nucleic acid encoding a modified IgG4 Fc fragment having a hinge region, which was mutated to include only one cysteine residue by the deletion of part of the amino acids in the hinge region, and a vector including the same.

The nucleic acid encoding the modified IgG4 Fc fragment of the present invention includes nucleic acids encoding the modified IgG4 Fc fragment including the amino acid sequence of SEQ ID NO: 2 (Pro-Ser-Cys-Pro-Ala-Pro-Glu-Phe-Leu-Gly-Gly-Pro-Ser-Val-Phe-Leu-Phe-Pro-Pro-Lys-Pro-Lys-Asp-Thr-Leu-Met-Ile-Ser-Arg-Thr-Pro-Glu-Val-Thr-Cys-Val-Val-Val-Asp-Val-Ser- Gln-Glu-Asp-Pro-Glu-Val-Gln-Phe-Asn-Trp-Tyr-Val-Asp-Gly-Val-Glu-Val-His-Asn-Ala-Lys-Thr-Lys-Pro-Arg-Glu-Glu-Gln-Phe-Asn-Ser-Thr-Tyr-Arg-Val-Val-Ser-Val-Leu-Thr-Val-Leu-His-Gln-Asp-Trp-Leu-Asn-Gly- Lys-Glu-Tyr-Lys-Cys-Lys-Val-Ser- Asn-Lys-Gly-Leu-Pro-Ser-Ser-Ile-Glu-Lys-Thr-Ile-Ser-Lys-Ala-Lys-Gly-Gln-Pro-Arg-Glu-Pro-Gln-Val-Tyr-Thr-Leu-Pro-Pro-Ser-Gln-Glu-Glu-Met-Thr-Lys-Asn-Gln-Val-Ser-Leu- Thr-Cys-Leu-Val-Lys-Gly-Phe-Tyr-Pro-Ser-Asp-Ile-Ala-Val-Glu-Trp-Glu-Ser-Asn-Gly-Gln-Pro-Glu-Asn-Asn-Tyr-Lys-Thr-Thr-Pro-Pro-Val-Leu-Asp-Ser-Asp-Gly-Ser-Phe-Phe-Leu-Tyr-Ser-Arg-Leu-Thr-Val-Asp-Lys- Ser-Arg-Trp-Gln-Glu-Gly-Asn-Val-Phe-Ser-Cys-Ser-Val-Met-His-Glu-Ala-Leu-His-Asn-His-Tyr-Thr-Gln-Lys-Ser-Leu-Ser-Leu-Ser-Leu-Gly-Lys). For example, the nucleic acid of the present invention may include the nucleotide sequence of SEQ ID NO: 3 (CCATCATGCCCAGCACCT-GAGTTCCTGGGGGGACCATCAGTCTTCCTG-TTCCCCC CAAAACCCAAGGACACCCTCAT-GATCTCCCGGACCCCTGAGGTCACATGCGTGG TGGTGGACGTGAGCCAGGAAGACCCTGAGG-TCCAGTTCAACTGGTACGTGGACG GCGTG-GAGGTGCATAATGCCAAGACAAAGCCGCGGGAG-GAGCAGTTCAACAGC ACGTACCGTGTGGTC-AGCGTCCTCACCGTCCTGCACCAGGACTGGCT-GAATGGCA AGGAGTACAAGTGCAAGGTCTC-CAACAAAGGCCTCCCATCCTCCATCGAGAAAA CCATCTCCAAAGCCAAAGGGCAGCCCCGAGAAC-CACAGGTGTACACCCTGCCCC CATCCCAGGAG-GAGATGACCAAGAACCAGGTCAGCCTGACCTG-CCTGGTCAAAG GCTTCTATCCCAGCGACATCGCC-GTGGAGTGGGAGAGCAATGGGCAGCCGGAGA ACAACTACAAGACCACGCCTCCCGTGCTGGAC-TCCGACGGCTCCTTCTTCCTCTA CAGCAGG-CTAACCGTGGACAAGAGCAGGTGGCAGGAGGG-GAACGTCTTCTCATG CTCCGTGATGCAT-GAGGCTCTGCACAACCACTACACACAGAA-GAGCCTCTCCCTG TCTCTGGGTAAA).

As used herein, the term "vector" refers to a recombinant vector capable of expressing a target protein in an appropriate host cell, which is a gene construct including regulatory factors operably linked to enable the expression of a gene insert.

As used herein, the term "operably linked" means that the regulatory sequence of a nucleic acid is functionally linked to the sequence of a nucleic acid encoding a target protein so that general functions can be performed. The operable linkage with the vector may be prepared by a genetic recombination technology well-known in the art, and site-specific DNA cleavage and linkage may be easily performed using enzymes, etc., generally well-known in the art. Appropriate expression vectors may include sequences for expression regulatory elements such as a promoter, a start codon, a termination codon, a polyadenylated signal, and an enhancer. The start codon and the termination codon should essentially exert their actions in an individual when a gene construct is inserted thereinto and should be in frame with the coding sequence. A general promoter may be constitutive or inducible. The expression vector may also include a selection marker for selecting a host cell including a vector, and for a replicable expression vector, it may include the origin of replication.

In another aspect, the present invention provides a microorganism, which is introduced with the above vector, capable of producing modified IgG4 Fc fragments.

For the purpose of the present invention, the microorganism is preferably a eukaryotic cell. The eukaryotic cell may be *Escherichia coli, Bacillus subtilis, Streptomyces, Pseudomonas, Proteus mirabilis, Staphylococcus*, etc., and preferably *Escherichia coli. Escherichia coli* may be *E. coli* XL-1 blue, *E. coli* BL21 (DE3), *E. coli* JM109, *E. coli* DH series, *E. coli* TOP10, and *E. coli* HB101, and more preferably *E. coli* BL21 (DE3), but is not limited thereto. When *E. coli* is used as a host cell, the Fc region of immunoglobulins can be produced in the form where the saccharides present in the CH2 domain of native immunoglobulins are originally deleted, because *E. coli* does not possess a system to conjugate glycans to proteins. Although the saccharides present in the CH2 domain of immunoglobulins do not affect the structural stability of immunoglobulins, it has been known that immunoglobulins can bind to Fc receptor-expressing cells and cause antibody-dependent cell cytotoxicity, induce immune cells to secrete cytokines, thereby causing inflammatory responses, and bind to the C1q element of complements and induce complement-fixing reactions. Accordingly, if the Fc regions of aglycosylated immunoglobulins are produced and conjugated to therapeutic proteins, the serum concentration of the therapeutic proteins can be maintained for a long period of time without inducing the effector functions of immunoglobulins.

The transformation method for the above vector in prokaryotic cells may include any method that can introduce nucleic acids into a cell, and the transformation may be performed by selecting a standard technology suitable for a given host cell known in the art. Examples of the method may include electroporation, protoplast fusion, calcium phosphate ($CaPO_4$) precipitation, calcium chloride ($CaCl_2$) precipitation, stirring using silicon carbide fibers, PEG, dextran sulfate, lipofectamine, etc., but are not limited thereto.

The microorganism introduced with the recombinant expression vector may be cultured according to a conventional method.

The culture process may be used after an easy adjustment according to the selected microorganism. Generally, the medium used for culture should contain all the nutrients essential for growth and survival of cells. The medium may contain various carbon sources, nitrogen sources, and trace element components. Examples of the carbon sources may include carbohydrates such as glucose, sucrose, lactose, fructose, maltose, starch, and cellulose; fats such as soybean oil, sunflower oil, castor oil, and coconut oil; fatty acids such as palmitic acid, stearic acid, and linoleic acid; alcohols such as glycerol and ethanol; and organic acids such as acetic acid. These carbon sources may be used alone or in combination. Examples of the nitrogen sources may include organic nitrogen sources such as peptone, yeast extract, meat gravy, malt extract, corn steep liquor (CSL), and soybean meal; and inorganic nitrogen sources such as urea, ammonium sulfate, ammonium chloride, ammonium phosphate, ammonium carbonate, and ammonium nitrate. These nitrogen sources may be used alone or in combination. In the above medium, dihydrogen phosphate, dipotassium hydrogen phosphate, and corresponding sodium-containing salts may be contained as phosphorus sources. Additionally, metal salts such as magnesium sulfate or iron sulfate may be contained. Furthermore, amino acids, vitamins, and appropriate precursors may also be contained. During the culture period, the pH of a culture may be adjusted by adding a compound such as ammonium hydroxide, potassium hydroxide, ammonia, phosphoric acid, and sulfuric acid to the culture in an appropriate manner. Additionally, during the culture period, an antifoaming agent, such as fatty acid polyglycol ester, may be added to prevent foam generation. Additionally, in order to maintain the aerobic state of the culture, oxygen or an oxygen-containing gas (e.g., air) may be injected into the culture. The culture temperature may generally be from 20° C. to 45° C., and preferably, from 25° C. to 40° C. Additionally, a fermentor may be used. When proteins are produced using a fermentor, various factors including the growth rate and the amount of expression products of a host cell should be considered. Protein expression may be induced by adding IPTG or the like in an appropriate culture condition. The modified IgG4 Fc fragment of the present invention may be overexpressed in a host cell in the form of an aggregate or may be expressed in an aqueous form. Regardless of their expression type, the proteins may be purified by a conventional protein purification method.

Accordingly, in another aspect, the present invention provides a method for preparing a modified IgG4 Fc fragment, and this method includes culturing a microorganism introduced with a nucleic acid encoding the modified IgG4 Fc fragment.

According to the above method, the industrial application of the above IgG4 Fc fragment, produced in a cell of a prokaryote such as *E. coli*, is not particularly limited. An exemplary application may be to use it as a carrier for the formation of a conjugate along with an arbitrary drug.

Accordingly, in another aspect, the present invention provides a drug and a drug conjugate in which the modified IgG4 Fc fragment is conjugated thereto by a linker.

As used herein, a drug conjugate or conjugate means that at least one drug is interconnected to at least one of the modified IgG4 Fc fragments.

As used herein, a drug refers to a material which can exhibit therapeutic activities when administered to humans or animals, and it may include a polypeptide, a compound, an extract, a nucleic acid, etc., but is not limited thereto. Preferably, the drug is a polypeptide drug.

As used herein, a physiologically active polypeptide drug, a polypeptide drug, and a protein drug are understood as having the same meaning, and they are characterized in that they are physiologically active types showing antagonism to various in vivo physiological phenomena.

The type of the conjugate in which the IgG4 Fc fragment is conjugated to a drug is not particularly limited, and the IgG4 Fc fragment and the drug may be conjugated at various ratios.

In the present invention, the linker may refer to both a peptide linker and a non-peptide linker, preferably a non-peptide linker, and more preferably a non-peptide polymer.

The non-peptide polymer refers to a biocompatible polymer to which at least two repeat units are conjugated, and the repeat units are interconnected by random covalent bonds other than peptide bonds. The non-peptide polymer may be selected from the group consisting of polyethylene glycol, polypropylene glycol, a copolymer between ethylene glycol and propylene glycol, polyoxyethylated polyol, polyvinyl alcohol, polysaccharide, dextran, polyvinyl ethyl ether, a biodegradable polymer such as polylactic acid (PLA) and polylactic-glycolic acid (PLGA), lipid polymer, chitins, hyaluronic acid, and a combination thereof, and preferably, polyethylene glycol. The derivatives known in the art and the derivatives that can easily be prepared using the technology in the art are also included in the scope of the present invention.

In the present invention, the non-peptide polymer may have two or three reactive ends, and the terminal reactive group of the non-peptide polymer is preferably selected from the group consisting of a reactive aldehyde group, a propionic aldehyde group, a butyl aldehyde group, a maleimide group, and a succinimide derivative. Examples of the succinimide derivative may include succinimidyl propionate, hydroxyl succinimidyl, succinimidyl carboxymethyl, and succinimidyl carbonate. In particular, when the non-peptide polymer includes a reactive aldehyde group at its end as a reactive group, it can minimize non-specific reactions and is effective in its respective binding to a physiological polypeptide and an immunoglobulin Fc fragment. The final product produced via reductive alkylation by aldehyde binding is more stable than that connected by amide bonding. The aldehyde reactive group reacts selectively in an N-terminus at low pH, and at high pH, e.g., pH 9.0, it may form a covalent bond with a lysine residue.

The terminal reactive groups of the non-peptide polymer may be the same or different with each other. For example, the non-peptide polymer may have a maleimide group at one end, while having an aldehyde group, a propionaldehyde group, or a butyl aldehyde group at the other end. When a polyethylene glycol or non-peptide polymer having a hydroxyl reactive group at both ends is used, the conjugate of the present invention may be prepared by activating the hydroxyl group with various reactive groups according to a known chemical reaction, or using polyethylene glycol having a modified reactive group which is commercially available.

As for the physiologically active polypeptides to be used by binding to the modified IgG4 Fc fragment of the present invention, anything that requires the increase of serum half-life may be used without limitation. For example, various physiologically active polypeptides, such as cytokines, interleukins, interleukin-binding proteins, enzymes, antibodies, growth factors, transcription regulatory factors, blood coagulation factors, vaccines, structural proteins, ligand proteins or receptors, cell surface antigens, receptor antagonists, derivatives thereof, and analogues thereof may be used.

Specifically, the physiologically active polypeptides may include human growth hormone, growth hormone-releasing hormone, growth hormone-releasing peptide, interferons and interferon receptors (e.g., interferon-α, -β, and -γ, soluble type I interferon receptor, etc.), colony-stimulating factors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, - 30, etc.) and interleukin receptors (e.g., IL-1 receptor, IL-4 receptor, etc.), enzymes (e.g., glucocerebrosidase, iduronate-2-sulfatase, α-galactosidase-A, agalsidase α, β, α-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin- and cytokine-binding proteins (e.g., IL-18 bp, TNF-binding protein, etc.), macrophage-activating factor, macrophage peptide, B cell factors, T cell factors, protein A, allergy inhibiting factors, necrosis glycoproteins, immunotoxins, lymphotoxins, tumor necrosis factors, tumor suppressors, transforming growth factors, α-1 antitrypsin, albumin, α-lactalbumin, apolipoprotein-E, erythropoietin, high-glycosylated erythropoietin, angiopoietins, hemoglobins, thrombin, thrombin receptor-activating peptide, thrombomodulin, blood coagulation factor VII, blood coagulation factor VIIa, blood coagulation factor VIII, coagulation factor IX, blood coagulation factor XIII, plasminogen activators, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone morphogenetic growth factor, bone morphogenetic protein, calcitonin, insulin and insulin derivative, atriopeptin, cartilage-inducing factor, elcatonin, connective tissue-activating factor, tissue factor pathway inhibitor, follicle-stimulating hormone, luteinizing hormone, luteinizing hormone-releasing hormone, nerve growth factors (e.g., nerve growth factor, ciliary neurotrophic factor, axogenesis factor-1, brain-natriuretic peptide, glial cell-derived neurotrophic factor, netrin, neutrophil inhibitor factor, neurotrophic factors, neutrin, etc.), parathyroid hormone, relaxin, secretin, somatomedin, insulin-like growth factor, adrenocortica hormone, glucagon, insulinotropic peptides including glucagon-like peptide-1 and exendin-4, incretins secreted in the intestines, adipocytes including leptons and neuro-cytokines effective for metabolic syndrome, cholecystokinin, pancreatic polypeptides, gastrin-releasing peptides, corticotropin-releasing factor, thyroid stimulating hormone, autotaxin, lactoferrin, myostatin, receptors (e.g., TNFR (P75), TNFR (P55), IL-1 receptor, VEGF receptor, B cell activating factor receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibody, polyclonal antibody, antibody fragments (e.g., scFv, Fab, Fab', F(ab')$_2$, and Fd), virus-derived vaccine antigen, etc., but are not limited thereto. The physiologically active polypeptide applicable in the present invention may be a native type; one which was produced by genetic recombination in a prokaryotic cell such as E. coli, or in a eukaryotic cell such as a yeast cell, an insect cell, or an animal cell; or a derivative which has an activity equivalent to the native type and a mutation in at least one amino acid position.

The modified IgG4 Fc fragment of the present invention may be produced in a cell after connecting it to a physiologically active polypeptide as a single gene sequence using a direct genetic recombination method, or the IgG4 Fc fragment may be produced independently and conjugated to a drug, such as a physiologically active polypeptide, in vitro.

In still another aspect, the present invention provides a pharmaceutical composition containing the above drug conjugate of the present invention as an active ingredient.

The pharmaceutical composition containing the conjugate of the present invention may include a pharmaceutically acceptable carrier. Examples of the pharmaceutically acceptable carrier may include a binder, a lubricant, a disintegrating agent, an excipient, a solubilizing agent, a dispersing agent, a stabilizing agent, a suspending agent, a coloring agent, a flavoring agent, etc.; for injection formulations, a buffering agent, a preserving agent, an analgesic, an isotonic agent, a stabilizing agent, etc., may be mixed for use; and for topical formulations, a base, an excipient, a lubricant, a preserving agent, etc., may be used.

The formulation type of the pharmaceutical composition according to the present invention may be prepared variously by combining with a pharmaceutically acceptable carrier. For example, for oral administration, the pharmaceutical composition may be formulated into tablets, troches, capsules, elixirs, suspensions, syrups, wafers, etc. For injections, the pharmaceutical composition may be formulated into single-dose ampoules or multidose containers. The pharmaceutical composition may be also formulated into solutions, suspensions, tablets, capsules, and sustained-release formulations.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition of the present invention may further contain a filler, an anti-coagulant, a lubricant, a humectant, a flavoring agent, an emulsifier, a preservative, etc.

In the present invention, the actual dose of the drugs where the IgG4 Fc fragment is used as a carrier will be determined based on the types of the drugs used as active ingredients along with various factors such as the disease to be treated, administration route, age, sex, and weight of a patient, severity of the disease, etc. Since the pharmaceutical composition of the present invention has excellent in vivo duration, the number and frequency of administration of the pharmaceutical formulation of the present invention can be significantly reduced.

The pharmaceutical formulation of the present invention may be administered via various routes.

As used herein, the term "administration" refers to an introduction of a particular material to a patient by an appropriate manner, and the conjugated drug of the present invention may be administered via any of the common routes as long as the drug can arrive at a target tissue. For example, intraperitoneal, intravenous, intramuscular, subcutaneous, intradermal, oral, topical, intranasal, intrapulmonary, and intrarectal administration may be performed, but the administration route is not limited thereto. However, since peptides are digested upon oral administration, active ingredients of a composition for oral administration should be coated or formulated for protection against degradation in the stomach. Preferably, the present composition may be administered in an injectable form. In addition, the pharmaceutical composition may be administered using a certain apparatus capable of transporting the active ingredients into a target cell.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1

Preparation of Human Granulocyte Colony-Stimulating Factor-PEG-Immunoglobulin Conjugate <1-1> Construction of a Vector Expressing an IgG4 Fc Domain For cloning of a heavy chain Fc region including the hinge region of IgG4, RT-PCR was performed using the blood cells collected from human blood as a template, as described below. First, total RNA was isolated from the blood of about pH 6, and the gene was amplified based on the RNA template using a Qiamp RNA blood kit (Qiagen). In particular, SEQ ID NO: 4 (gggcatatgc catcatgccc agcacctgag ttcctgggg) and SEQ ID NO: 5 (gggggatccc tatttaccca gagacaggga ga) pair were used as primers. To facilitate the subsequent process, a domain capable of recognizing NdeI restriction sites and ATG, the start codon necessary for protein expression was inserted into the primers, and a domain capable of recognizing BamHI restriction sites was inserted into the 3-primer of SEQ ID NO: 5. The Fc region product amplified therefrom was cleaved with NdeI and BamHI, respectively, and subcloned into pET22b (Novagen Co., Ltd.) to prepare a plasmid. The plasmid was designed so that the IgG4 Fc fragment can include a hinge sequence, where the amino acid residues at the $1^{st}$ to $8^{th}$ positions of the entire amino acid sequence of Glu-Ser-Lys-Tyr-Gly-Pro-Pro-Cys-Pro-Ser-Cys-Pro in the IgG4 Fc hinge are deleted.

The plasmid prepared in this Example was named as "pmHMC001", and the result of its sequence analysis showed that the nucleic acid encoding the IgG4 Fc fragment has a nucleotide sequence of SEQ ID NO: 3, and the IgG4 Fc fragment has the amino acid sequence of SEQ ID NO: 2 at the time of expression.

The thus-prepared expression vector was transformed into *E. coli* BL21 (DE3) and thereby an *E. coli* transformant, *E. coli* BL21/pmHMC001 (HMC001), was prepared.

<1-2> Expression and Purification of an IgG4 Fc Region

The microorganism transformant obtained in Example <1-1> was inoculated into a fermentor (Marubishi Co., Ltd.) to be fermented, and the expression of the IgG4 Fc fragment was examined.

First, the above transformants placed in 100 mL of LB medium were cultured in a shaking water bath overnight and then inoculated into a fermentor to proceed with the culture. The fermentor was maintained at 35° C. or 28° C., and the culture was begun by shaking at 500 rpm while supplying air thereinto at 20 vvm for preventing the condition therein from becoming anaerobic. With the progress of the fermentation, the energy sources which were deficient for the growth of the microorganism were replenished using glucose and yeast extract according to the fermentation state of the microorganism, and the expression was induced by adding IPTG, an inducer, thereto when the OD at 600 nm reached 80. The culture was processed for 40 hours to 45 hours until the OD at 600 nm reached the range of 100 to 120 in order to obtain a high concentration culture.

The expression of IgG4 Fc in an *E. coli* transformant was confirmed by an experiment described below.

In order to confirm the complete expression of IgG4 Fc in cytoplasm, part of the fermentation liquid was mixed with an equal amount of a 2× protein drip buffer and electrophoresed in a 15% SDS-PAGE (Criterion Gel, Bio-Rad). As a result, it was confirmed that IgG Fc was overexpressed in the prepared transformant. The overexpressed protein was shown to form coagulants, and the protein was purified via refolding and performance of a column of the coagulants in the same manner First, 10 g of cells were dissolved in 100 mL of a lysis buffer (10 mM Tris, pH 9.0, 1 mM EDTA, 0.5% Triton X-100, and 0.2 M NaCl) and then subjected to ultra-sonication. The resultant was subjected to centrifugation at 10,000 rpm for 20 minutes to be separated into a soluble fraction and an insoluble fraction, and 2 g of the insoluble coagulant was dissolved in 20 mL of a solubilization buffer (6 M guanidine and 50 mM Tris) and then allowed to react for 30 minutes at 4 with gentle shaking. Upon completion of the reaction, the resultant was diluted by adding 10 volumes of a refolding buffer (2 M urea, 50 mM Tris, 0.25 M arginine, and 3 mM cysteine, pH 9.0) and then allowed to react overnight with gentle shaking. Upon completion of the reaction, the sample was provided with a fresh 10 mM Tris-HCl (pH 8.0) buffer using Sephadex G25. The sample with a replaced buffer was eluted in a concentration gradient of Tris-HCl (pH 8.0) and NaCl using DEAE-FF (GE healthcare), and phenyl-FF (GE healthcare) was eluted with a concentration gradient of ammonium sulfate and 10 mM Tris-HCl (pH 7.5) in order to remove a large amount of multimers and monomers. For the subsequent column process, the resultant was desalinized with 10 mM Tris (pH 7.5) using Sephadex G25 (GE healthcare), and then, in order to obtain high purity IgG4 Fc, 15Q (GE healthcare) was eluted with a concentration gradient of 10 mM Tris-HCl (pH 7.5) and NaCl, and finally IgG4 Fc was obtained.

<1-3> Preparation of a Drug Conjugate I

1) Preparation of a Conjugate Between Granulocyte Colony-Stimulating Factors and PEG ALD-PEG-ALD (Shearwater Inc., USA), a poly(ethylene glycol) having a molecular weight of 3.4 kDa with aldehyde reactive groups at both ends, was added into a 100 mM phosphate buffer in which granulocyte colony-stimulating factors were dissolved at a concentration 5 mg/mL, so that the molar ratio of the granulocyte colony-stimulating factors:PEG became 1:5. Sodium cyanoborohydride (NaCNBH$_3$), a reducing agent, was added to a final concentration of 20 mM thereto, and reacted for 3 hours at 4 while stirring slowly. In order to obtain a conjugate in which PEG is selectively conjugated to the amino terminus of the granulocyte colony-stimulating factors and PEG and the granulocyte colony-stimulating factors are conjugated at a ratio of 1:1, the reaction mixture was subjected to a Superdex size exclusion chromatography (Superdex R, Pharmacia, USA). The colony-stimulating factors were purified using 10 mM potassium-phosphate buffer (pH 6.0) as an elution solution, whereas the granulocyte colony-stimulating factors which were not conjugated to PEG, unreacted PEG, and dimer byproducts, where two granulocyte colony-stimulating factors were conjugated to PEG were removed. The purified granulocyte colony-stimulating factor-PEG conjugate was concentrated to 5 mg/mL.

2) Formation of a Conjugate Between a Granulocyte Colony-Stimulating Factor-PEG Conjugate and an IgG4 Fc Fragment The IgG4 Fc fragment of the present invention was dissolved in 100 mM phosphate buffer. In order to conjugate the IgG4 Fc fragment to the aldehyde reactive groups of the granulocyte colony-stimulating factor-PEG conjugate purified above, the granulocyte colony-stimulating factor-PEG conjugate was added to an IgG4 Fc fragment-containing buffer so that the molar ratio of granulocyte colony-stimulating factor-PEG conjugate:IgG4 Fc fragment became 1:5. Sodium cyanoborohydride (NaCNBH$_3$), a reducing agent, was added thereto for a final concentration of 20 mM, and the reaction mixture was reacted for 20 hours at 4 while stirring slowly. Upon completion of conjugation reaction, unreacted materials and byproducts were removed, and the granulocyte colony-stimulating factor-PEG-immunoglobulin protein conjugate was purified by anion exchange chromatography. The granulocyte colony-stimulating factor-PEG-IgG4 Fc fragment conjugate was purified by adding the above reaction mixture to a DEAE column (Pharmacia, USA), which was equilibrated with 20 mM Tris buffer (pH 7.5), followed by flowing the same buffer containing 1 M NaCl with a linear concentration gradient method (NaCl concentration: 0 M→0.5 M). To remove a small amount of unreacted immunoglobulins and human growth hormone mixed as impurities with the fraction of the thus-obtained granulocyte colony-stimulating factor-PEG-IgG4 Fc fragment, cation exchange chromatography was additionally performed. The fraction of the granulocyte colony-stimulating factor-PEG-IgG4 Fc fragment was added into a polyCAT column (PolyLC, USA), which was equilibrated with 10 mM sodium acetate (pH 4.5), and additionally purified by flowing 10 mM sodium acetate (pH 4.5) buffer containing 1 M NaCl thereon with a linear concentration gradient method (NaCl concentration: 0 M→0.5 M), and thereby the granulocyte colony-stimulating factor-PEG-IgG4 Fc fragment conjugate (HM10460A) was obtained with purity.

Example 2

Confirmation of Chain Exchange Between Human Granulocyte Colony-Stimulating Factor-PEG-Immunoglobulin Conjugate and Human IgG4 in Rat Blood Human IgG4 in the amount of 2 mg was biotin-labeled by mixing with 20 mg/mL of biotin-7-NHL solution at a molecule ratio of 1:10 and purified with a Biotin Protein Labeling Kit (Roche). The blood collected from normal rats was treated with heparin for anticoagulation purposes and added with penicillin-streptomycin (1% v/v). 1.5 mg of biotin-labeled IgG4 and 1.32 mg of HM10460A were added into 3 mL of the blood, mixed together, and the mixture was aliquoted into 6 tubes (0.5 mL/tube) and incubated in a 37° C. incubator. One tube was taken out at times of 0 hours, 4 hours, 10 hours, 24 hours, and 48 hours, respectively, and plasma was separated therefrom and stored at −20° C. Each of the plasma samples and standard materials were mixed with a non-reducing protein sample buffer, and the resultant was subjected to an SDS-PAGE using a 4% to 15% concentration gradient polyacrylamide gel. Biotin-labeled IgG4 and HM10460A were used as standard materials. The gel, upon completion of electrophoresis, was blotted onto a PVDF membrane (Immobilon-P, MILLIPORE) and analyzed using anti-human GCSF antibodies and streptavidin-HRP. Regarding the antibody binding conditions, anti-human IgG Fc antibodies (Sigma) were used in 5% skim milk blocking condition after diluting at a ratio of 1:150000, anti-human GCSF antibodies (Human G-CSF Assay Kit. IBL) in 1% skim milk blocking condition after diluting at a ratio of 1:2000, and streptavidin-HRP in 5% skim milk blocking condition after diluting at a ratio of 1:5000, respectively. HM10460A was confirmed to form dimers (94 kDa), which have two G-CSFs per each IgG4 Fc fragment, and IgG4 Fc fragments (50 kDa), by the chain exchange mechanism between HM10460A themselves.

In contrast, when HM10460A induced a mutual chain exchange reaction between HM10460A and human IgG4, molecules with a size of 100 kDa and 122 kDa were expected to form. However, these molecules were not observed by Western blot analysis. In contrast, when analyzed via streptavidin-HRP, a 75 kDa band appeared on the human IgG4 lane, and this confirms the formation of monomers from human IgG4, which is itself a dimer of the human IgG4 by nature (FIG. 1).

Example 3

Confirmation of Chain Exchange Between Human Granulocyte Colony-Stimulating Factor-PEG-Immunoglobulin Conjugate and Human IgG4 in Human Blood To human blood collected from a donor was added penicillin-streptomycin (1% v/v). 1.32 mg of the HM10460A prepared in Example 1 was mixed with 3 mL of the blood, and the mixture was aliquoted into 6 tubes (0.5 mL/tube) and incubated in a 37° C. incubator. One tube was taken out at times of 0 hours, 4 hours, 10 hours, 24 hours, and 48 hours, respectively, and plasma was separated therefrom and stored at −20° C. prior to analysis. Each of the plasma samples and HM10460A and an IgG4 Fc fragment at varied concentrations as control materials were mixed with a non-reducing protein sample buffer, and the resultant was subjected to an SDS-PAGE using a 4% to 15% concentration gradient polyacrylamide gel. The gel, upon completion of electrophoresis, was blotted onto a PVDF membrane (Immobilon-P, MILLIPORE) and analyzed using anti-human GCSF antibodies. The anti-human G-CSF antibodies (Human G-CSF Assay Kit. IBL) were used in a 1% skim milk blocking condition after diluting at a ratio of 1:2000. As in the rat blood, the molecules with a size of 100 kDa and 122 kD, which may be formed by chain exchange with human IgG4, were not formed (FIG. 2).

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

---

The invention claimed is:

1. A modified aglycosylated IgG4 Fc fragment comprising a modified hinge region,
wherein the modified hinge region consists of the amino acid sequence selected from the group consisting of amino acid sequences of SEQ ID NOs: 4, 8, 10, 11, 12, 14, 15, 19, 20, and 21, and includes only one cysteine residue,
wherein in vivo chain exchange and monomer formation do not occur.

2. A modified IgG4 Fc fragment consisting of the amino acid sequence of SEQ ID NO: 2.

3. The modified IgG4 Fc fragment of claim 1, which is modified by a nonpeptidyl polymer.

4. A method of preparing the IgG4 Fc fragment according to claim 1 comprising culturing a microorganism introduced with a vector comprising a nucleic acid encoding any one of the IgG4 Fc fragment of claim 1.

5. A drug conjugate comprising any one of the modified aglycosylated IgG4 Fc fragment according to claim 1 and a drug, wherein the drug is conjugated to the Fc via a linker.

6. The drug conjugate of claim 5, wherein the drug is selected from the group consisting of human growth hormone, growth hormone-releasing hormone, growth hormone-releasing peptide, interferon, interferon receptor, colony-stimulating factor, interleukin, interleukin receptor, enzyme, interleukin- and cytokine-binding protein, macrophage-activating factor, macrophage peptide, B cell factor, T cell factor, necrosis glycoprotein, immunotoxin, lymphotoxin, tumor necrosis factor, tumor suppressor, transforming growth factor, α-1 antitrypsin, albumin, α-lactalbumin, apolipoprotein-E, erythropoietin, high-glycosylated erythropoietin, angiopoietin, hemoglobin, thrombin, thrombin receptoractivating peptide, thrombomodulin, blood coagulation factor VII, blood coagulation factor VIIa, blood coagulation factor VIII, coagulation factor IX, blood coagulation factor XIII, plasminogen activator, fibrin-binding peptide, urokinase, streptokinase, hirudin, protein C, C-reactive protein, superoxide dismutase, leptin, platelet-derived growth factor, epithelial growth factor, epidermal growth factor, angiostatin, angiotensin, bone morphogenetic growth factor, bone morphogenetic protein, calcitonin, insulin, atriopeptin, cartilage-inducing factor, elcatonin, connective tissue-activating factor, follicle-stimulating hormone, luteinizing hormone, luteinizing hormone-releasing hormone, nerve growth factor, ciliary neurotrophic factor, axogenesis factor-1, brain-natriuretic peptide, glial cell-derived neurotrophic factor, netrin, neutrophil inhibitor factor, neurotrophic factor, neutrin, parathyroid hormone, relaxin, secretin, somatomedin, insulin-like growth factor, adrenocorticahormone, glucagon, insulinotropic peptide, glucagon-like peptide-1, exendin 4, incretin, neuro-cytokine effective for metabolic syndrome, cholecystokinin, pancreatic polypeptide, gastrin-releasing peptide, corticotropin-releasing factor, thyroid stimulating hormone, autotaxin, lactoferrin, myostatin, receptor, and cell surface antigen.

7. The drug conjugate of claim 5, wherein the drug is a granulocyte colony-stimulating factor.

8. The drug conjugate of claim 5, wherein the linker is a nonpeptidyl polymer.

9. The drug conjugate of claim 8, wherein the nonpeptidyl polymer has two or three reactive ends.

10. A pharmaceutical composition comprising the conjugate of claim 5.

11. A drug carrier comprising any one of the modified aglycosylated IgG4 Fc fragments comprising a modified hinge region of claim 1.

12. A drug carrier comprising the modified aglycosylated IgG4 Fc fragment according to claim 2.

* * * * *

SEQUENCE LISTING

<160> NUMBER OF SEQ ID NOS: 21

<210> SEQ ID NO 1
<211> LENGTH: 12
<212> TYPE: PRT
<213> ORGANISM: HOMO SAPIENS

<400> SEQUENCE: 1

Glu Ser Lys Tyr Gly Pro Pro Cys Pro Ser Cys Pro
1               5                   10

<210> SEQ ID NO 2
<211> LENGTH: 221
<212> TYPE: PRT
<213> ORGANISM: HOMO SAPIENS

<400> SEQUENCE: 2

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser Gln Glu Asp Pro Glu Val Gln
            35                  40                  45

Phe Asn Trp Tyr Val Asp Gly Val Glu Val His Asn Ala Lys Thr Lys
        50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220

<210> SEQ ID NO 3

<211> LENGTH: 663
<212> TYPE: DNA
<213> ORGANISM: HOMO SAPIENS

<400> SEQUENCE: 3

```
ccatcatgcc cagcacctga gttcctgggg ggaccatcag tcttcctgtt ccccccaaaa      60
cccaaggaca ccctcatgat ctcccggacc cctgaggtca catgcgtggt ggtggacgtg     120
agccaggaag accctgaggt ccagttcaac tggtacgtgg acggcgtgga ggtgcataat     180
gccaagacaa agccgcggga ggagcagttc aacagcacgt accgtgtggt cagcgtcctc     240
accgtcctgc accaggactg gctgaatggc aaggagtaca agtgcaaggt ctccaacaaa     300
ggcctcccat cctccatcga gaaaaccatc tccaaagcca agggcagccc cgagaaccca     360
caggtgtaca ccctgccccc atcccaggag gagatgacca gaaccaggt cagcctgacc      420
tgcctggtca aaggcttcta tcccagcgac atcgccgtgg agtgggagag caatgggcag     480
ccggagaaca actacaagac cacgcctccc gtgctggact ccgacggctc cttcttcctc     540
tacagcaggc taaccgtgga caagagcagg tggcaggagg ggaacgtctt ctcatgctcc     600
gtgatgcatg aggctctgca caaccactac acacagaaga gcctctccct gtctctgggt     660
aaa                                                                   663
```

<210> SEQ ID NO 4
<211> LENGTH: 11
<212> TYPE: PRT
<213> ORGANISM: Artificial Sequence
<220> FEATURE:
<223> OTHER INFORMATION: Variant of hinge region

<400> SEQUENCE: 4

Glu Ser Lys Tyr Gly Pro Pro Pro Ser Cys Pro
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Variant of hinge region

<400> SEQUENCE: 5

Glu Ser Lys Tyr Gly Pro Pro Cys Pro Ser Pro
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Variant of hinge region

<400> SEQUENCE: 6

Glu Ser Lys Tyr Gly Pro Pro Cys Pro Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Variant of hinge region

<400> SEQUENCE: 7

```
Glu Ser Lys Tyr Gly Pro Pro Cys Pro Pro
1               5                   10
```

<210> SEQ ID NO 8
<211> LENGTH: 8
<212> TYPE: PRT
<213> ORGANISM: Artificial Sequence
<220> FEATURE:
<223> OTHER INFORMATION: Variant of hinge region

<400> SEQUENCE: 8

```
Lys Tyr Gly Pro Pro Cys Pro Ser
1               5
```

<210> SEQ ID NO 9
<211> LENGTH: 8
<212> TYPE: PRT
<213> ORGANISM: Artificial Sequence
<220> FEATURE:
<223> OTHER INFORMATION: Variant of hinge region

<400> SEQUENCE: 9

```
Glu Ser Lys Tyr Gly Pro Pro Cys
1               5
```

<210> SEQ ID NO 10
<211> LENGTH: 7
<212> TYPE: PRT
<213> ORGANISM: Artificial Sequence
<220> FEATURE:
<223> OTHER INFORMATION: Variant of hinge region

<400> SEQUENCE: 10

```
Glu Lys Tyr Gly Pro Pro Cys
1               5
```

<210> SEQ ID NO 11
<211> LENGTH: 6
<212> TYPE: PRT
<213> ORGANISM: Artificial Sequence
<220> FEATURE:
<223> OTHER INFORMATION: Variant of hinge region

<400> SEQUENCE: 11

```
Glu Ser Pro Ser Cys Pro
1               5
```

<210> SEQ ID NO 12
<211> LENGTH: 5
<212> TYPE: PRT
<213> ORGANISM: Artificial Sequence
<220> FEATURE:
<223> OTHER INFORMATION: Variant of hinge region

<400> SEQUENCE: 12

```
Glu Pro Ser Cys Pro
1               5
```

<210> SEQ ID NO 13
<211> LENGTH: 4
<212> TYPE: PRT
<213> ORGANISM: Artificial Sequence
<220> FEATURE:
<223> OTHER INFORMATION: Variant of hinge region

<400> SEQUENCE: 13

```
Pro Ser Cys Pro
```

```
<210> SEQ ID NO 14
<211> LENGTH: 10
<212> TYPE: PRT
<213> ORGANISM: Artificial Sequence
<220> FEATURE:
<223> OTHER INFORMATION: Variant of hinge region

<400> SEQUENCE: 14

Glu Ser Lys Tyr Gly Pro Pro Ser Cys Pro
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Variant of hinge region

<400> SEQUENCE: 15

Lys Tyr Gly Pro Pro Pro Ser Cys Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Variant of hinge region

<400> SEQUENCE: 16

Glu Ser Lys Tyr Gly Pro Ser Cys Pro
1               5

<210> SEQ ID NO 17
<211> LENGTH: 8
<212> TYPE: PRT
<213> ORGANISM: Artificial Sequence
<220> FEATURE:
<223> OTHER INFORMATION: Variant of hinge region

<400> SEQUENCE: 17

Glu Ser Lys Tyr Gly Pro Pro Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Variant of hinge region

<400> SEQUENCE: 18

Lys Tyr Gly Pro Pro Cys Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Variant of hinge region

<400> SEQUENCE: 19

Glu Ser Lys Pro Ser Cys Pro
1               5
```

```
<210> SEQ ID NO 20
<211> LENGTH: 6
<212> TYPE: PRT
<213> ORGANISM: Artificial Sequence
<220> FEATURE:
<223> OTHER INFORMATION: Variant of hinge region

<400> SEQUENCE: 20

Glu Ser Pro Ser Cys Pro
1               5

<210> SEQ ID NO 21
<211> LENGTH: 4
<212> TYPE: PRT
<213> ORGANISM: Artificial Sequence
<220> FEATURE:
<223> OTHER INFORMATION: Variant of hinge region

<400> SEQUENCE: 21

Glu Pro Ser Cys
1
```